(12) United States Patent
Avni et al.

(10) Patent No.: US 7,998,092 B2
(45) Date of Patent: Aug. 16, 2011

(54) FORCE SENSOR SYSTEM FOR USE IN MONITORING WEIGHT BEARING

(75) Inventors: Arik Avni, Meitar (IL); Lior Bar-Nes, Lehavim (IL); Ronit Frideman, Lehavim (IL)

(73) Assignee: Andante Medical Devices, Ltd. (IL)

( * ) Notice: Subject to any disclaimer, the term of this patent is extended or adjusted under 35 U.S.C. 154(b) by 1344 days.

(21) Appl. No.: 10/520,965

(22) PCT Filed: Jul. 10, 2003

(86) PCT No.: PCT/IL03/00572
§ 371 (c)(1),
(2), (4) Date: Jun. 12, 2006

(87) PCT Pub. No.: WO2004/008095
PCT Pub. Date: Jan. 22, 2004

(65) Prior Publication Data
US 2006/0282017 A1 Dec. 14, 2006

Related U.S. Application Data

(60) Provisional application No. 60/395,127, filed on Jul. 11, 2002.

(51) Int. Cl.
*A61H 3/00* (2006.01)
(52) U.S. Cl. ......... 600/587; 607/48; 607/115; 607/144
(58) Field of Classification Search ............. 607/2, 48, 607/49, 66, 77, 115, 144, 149; 600/587, 600/592, 595, 390, 391; 128/133, 905, 134, 128/135, 68.1, 82.1, 378, 594, 382
See application file for complete search history.

(56) References Cited

U.S. PATENT DOCUMENTS 2,095,268 A 10/1937 Alonzo
(Continued)

FOREIGN PATENT DOCUMENTS

DE 3631923 A1 3/1988
(Continued)

OTHER PUBLICATIONS

Chae, et al., "Neuromuscular Stimulation for Motor Relearning in Hemiplegia", *Critical Reviews in Physical and Rehabilitation Medicine*, 1999, 11, 279-297.

(Continued)

*Primary Examiner* — Mark W Bockelman
*Assistant Examiner* — Erica Lee
(74) *Attorney, Agent, or Firm* — Woodcock Washburn LLP

(57) ABSTRACT

A force sensor system for use in monitoring weight bearing on a location. The force sensor system comprises at least one a foot force sensor, a palm force sensor, and a knee force sensor. The foot force sensor comprises a flexible insole containing a plurality of inflatable pockets that are inflated with air or liquid. The palm force sensor and knee force sensor each comprise a wrap to be worn around the palm and knee, respectively. Each wrap comprises a pocket. Each pocket is connected to a tube that, in turn, connects with a pressure sensor and a connector coupling that is remote from the pocket. Each coupling contains a valve. The valve opens to allow inflation and deflation of each inflatable pocket. The pressure sensors measure the air or liquid pressure within each of the inflatable pockets, and convert the corresponding pressure signal into a suitable output signal medium, usually electrical signals. The output signal from the sensors provides accurate real time input data to a weight bearing biofeedback system or to control a stimulator for activation of an electronic orthosis to normalize dynamic gait patterns.

18 Claims, 9 Drawing Sheets

U.S. PATENT DOCUMENTS

| | | | |
|---|---|---|---|
| 3,305,036 A | 2/1967 | Walters | |
| 3,791,375 A | 2/1974 | Pfeiffer | 128/2 |
| 3,881,496 A * | 5/1975 | Vredenbregt et al. | 607/49 |
| 3,974,491 A | 8/1976 | Sipe | 340/272 |
| 4,426,884 A | 1/1984 | Polchaninoff | 73/172 |
| 4,610,253 A | 9/1986 | Rosenberg | |
| 4,734,034 A | 3/1988 | Maness et al. | 433/68 |
| 4,745,930 A | 5/1988 | Confer | 128/779 |
| 4,813,436 A | 3/1989 | Au | 128/779 |
| 4,856,993 A | 8/1989 | Maness et al. | 433/68 |
| 4,949,729 A | 8/1990 | Haski | 128/774 |
| 4,989,615 A * | 2/1991 | Hochberg | 600/587 |
| 5,005,140 A * | 4/1991 | Havriluk | 702/139 |
| 5,033,291 A | 7/1991 | Podoloff et al. | 73/172 |
| 5,107,854 A | 4/1992 | Knotts et al. | 128/779 |
| 5,131,408 A | 7/1992 | Smith | 128/774 |
| 5,655,316 A | 8/1997 | Huang | 36/132 |
| 5,775,332 A * | 7/1998 | Goldman | 600/587 |
| 5,813,142 A | 9/1998 | Demon | 36/29 |
| 6,036,660 A * | 3/2000 | Toms | 600/595 |
| 6,145,142 A * | 11/2000 | Rechin et al. | 5/706 |
| 6,273,863 B1 | 8/2001 | Avni | |
| 2003/0036771 A1 * | 2/2003 | McEwen et al. | 606/202 |

FOREIGN PATENT DOCUMENTS

| | | |
|---|---|---|
| FR | 2720622 B1 | 12/1995 |
| WO | WO 9113575 | 9/1991 |
| WO | WO 0016689 | 3/2000 |
| WO | WO 0136051 A2 | 5/2001 |

OTHER PUBLICATIONS

Granat, et al., "Peroneal Stimulator: Evaluation for the Correction of Spastic Drop Foot in Hemiplegia", *Arch Phys Med Rehab*, 1996, 77, 19-24.

Liberson, et al., "Functional Electrotherapy, Stimulation of the Peroneal Nerve Synchronized with the Swing Phase of Gait of Hemiplegic Patients", *Arch Phys Med Rehab*, 1961, 42, 101-105.

* cited by examiner

FORCE SENSOR SYSTEM FOR USE IN MONITORING WEIGHT BEARING

BACKGROUND OF THE INVENTION

1. Field of the Invention

The present invention relates to an ergonomically designed force sensor system suitable for monitoring weight bearing or temporal parameters on different body regions, such as the foot, knee, and palm. The sensor system may be used in a weight bearing biofeedback system or a functional electrical stimulation system. The foot sensor system may be connected to a portable control unit including a weight bearing program for neurologic, orthopedic or pediatric gait rehabilitation and/or used in connection with a two channel peroneal stimulator for controlling the lower leg muscles to normalize dynamic walking patterns. On the other hand, the knee and palm sensor systems may be used in a weight bearing feedback system in physical stimulation of neurologic and pediatric injuries or for controlling an electronic orthosis.

2. Description of the Prior Art

Stroke is the leading cause of disability in the elderly and a significant source of disability in younger adults. More than 700,000 strokes occur each year, with a prevalence of approximately 3 million. Although stroke is uncommon under the age of 50, the incidence of stroke doubles with each decade after the age of 55. Nearly a third of all stroke survivors will have significant residual disability, with older individuals generally experiencing slower functional recovery. The economic burden associated with stroke is estimated to be more than $30 billion in health care costs and lost productivity each year, making stroke one of the most expensive illnesses in the United States (Chae et al., "Neuromuscular Stimulation for Motor Relearning in Hemiplegia. Critical Reviews in Physical and Rehabilitation Medicine, 11:279-297, 1999).

Hemiparesis due to stroke often results in spastic drop-foot (i.e., the loss of ability to dorsiflex the foot on the affected side). One approach to the management of spastic drop-foot is the prescription of an ankle foot orthosis (AFO), which holds the foot in a neutral position to prevent it from dragging during the swing phase of gait. An alternative approach is active stimulation of the dorsi and plantar flexors.

Electrical stimulation for correction of spastic drop foot in hemiplegia was just applied by Liberson and coworkers in 1961 (Liberson et. al., Functional Electrotherapy, Stimulation of the Peroneal Nerve Synchronized with the Swing Phase of Gait of Hemiplegic Patients. Arch Phys Med Rehab, 42:101-105, 1961). Surface electrodes were applied over the peroneal nerve at the head of the fibula. A stimulator worn around the waist was controlled by a footswitch in the heel of the shoe of the affected limb. When the patient lifted the heel to take a step, the stimulator was activated. Stimulation was stopped when the heel contacted the ground. This system, the peroneal stimulator (PS), produces dorsiflexion and eversion of the foot during the swing phase of gait (Granat et al. Peroneal Stimulator: Evaluation for the Correction of Spastic Drop Foot in Hemiplegia. Arch Phys Med Rehab, 77:19-24, 1996). This system and other electrical stimulation systems are dependent on a sensor system to accurately sense when and to measure how much force is being applied to a region or regions of the foot.

There are a number of insole foot force sensing devices currently used for measuring force on the foot. For example, U.S. Pat. No. 4,745,930 discloses a flexible force sensing insole which incorporates multiple electrical switches which close after a certain threshold level of force is imposed on the insole. U.S. Pat. No. 5,033,291 discloses a force sensing device which uses a plurality of intersecting electrodes. The electrodes act as open circuit switches at each intersection which close when force is applied to the insole at that intersection location. The resistance between the two electrodes varies with the amount of force applied. U.S. Pat. No. 4,426,884 discloses a flexible force sensor which acts as an open circuit, closing with the application of force on the sensor and having resistance that varies with the amount of force.

All of the known foot force measurement devices function to convert mechanical force into a suitable signal medium, usually electrical signals. Consequently, the devices can be conveniently categorized according to the type of sensor used to convert changes in mechanical force to changes in electrical signals. These types of sensors include switches, strain gauge sensors that respond to mechanical deformation, single direct electronic force sensors, multiple direct electronic force sensors with random spacing, and multiple direct electronic force sensors with regular spacing. The sensors which measure mechanical deformation of structural elements supporting the wearer's foot by use of electrical wire or ribbon type strain gauges accurately measure weight, but they are also disadvantageous because of their bulk and weight.

The multiple direct electronic force sensor system taught in U.S. Pat. No. 4,813,436 to Au measures forces only where the individual sensors are attached to the foot. If the measurements are used to compute total force applied to the foot and are variously spaced, the contributory area of each sensor must be used in the necessary computation of the total force applied. This system is disadvantageous in that the relative position of each sensor must be separately determined for each person on which the sensor is used. This problem is solved by the multiple direct electronic force sensors taught in U.S. Pat. Nos. 4,734,034, 4,856,993 and 5,033,291 to Maness et al. in which the sensors are regularly spaced. Since the relative position of each sensor is fixed, a mathematical position of the location of each sensor can easily be made to be part of a permanent computer database. These sensor arrays are very thin and very light weight, but they cannot conform to a compound curved surface without wrinkling. Such wrinkled or folded thin film sensor arrays will produce erroneous results. For example, if the sensor array is folded so that two separate sensors are positioned one above the other, they both measure the same force. This is an obvious error. A folded sensor array also may produce an electrical signal from the folding alone, another obvious error. Folding or wrinkling also subjects the sensor array to severe fatigue stress, which can lead to early and sudden failure.

U.S. Pat. No. 3,881,496 issued to Vrendenbregt et al. discloses an apparatus and method for electrically stimulating leg muscles using an air-filled chamber located in the sole of the shoe beneath the ball of the foot. The chamber is coupled through an air channel or a thin hose and a diaphragma to a microswitch located in the heel. The switch activates an electric pulse generator in synchronism with the normal walking pattern.

U.S. Pat. No. 3,974,491 issued to Sipe discloses a sensor having a fluid filled chamber that is a continuous, resilient tube having a circular cross section. The tube is coiled under the heel and the sole of a patient's foot inside a sponge rubber footpad. The footpad is between adhesive sheets of flexible, dimensionally stable material such as rubber-coated fabric. The foot pad does not measure the total load placed on the limb because a portion of that load is done by a sponge rubber pad and because the tube is not directly beneath all parts of the foot.

U.S. Pat. No. 5,107,854 issued to Knotts et al. discloses a single fluid filled plantar chamber that supports the entire load borne by a patient's foot. The plantar chamber is connected to a remote pressure sensing device that is responsive to pressure changes transmitted by the single fluid filled plantar chamber. The sensing device disclosed by Knotts et al. provides an accurate measurement of the force on the foot because the remote pressure sensor is not positioned in the insole, and, therefore, is not subject to the problem of electrical contact failure While the sensing device disclosed by Knotts et al. provides an accurate measurement of the force on the foot, it comprises only a single chamber that is used to provide a single force measurement. In the course of rehabilitating the foot, however, it is often desirable to obtain force measurements from a plurality of locations on the foot such as, for example, the heel region and the toe region. U.S. Pat. No. 3,791,375 issued to Pfeiffer discloses a remote displacement measuring device that is connected to two units, a heel unit and a toe unit, located in the insole. The units deflect and change their volume in accordance with the amount of load placed thereon. The displacement measuring device is signaled with an electrical alarm to indicate when a predetermined load on the units is reached. The displacement measuring device consists of a single sensor such as, for example, a bellows that measures the combined total displacement from both the heel and the toe unit.

While the sensing device disclosed by Pfeiffer provides an accurate single measurement of two regions of the foot, it comprises only a single sensing device that is used to obtain a cumulative single measurement. In addition to measuring the cumulative force on a plurality of regions of the foot, it is also desirable to obtain and compare a plurality of measurements, each from a different location of the foot. Additionally, it is desirable to obtain such measurements using sensors that are remote from the insole. Sensors within an insole are subject to the problem of electrical contact failure, and an awkward placement or posture of the foot may result in a failure to activate insole sensors. The electronic components in existing insoles increase the size of the insole, causing blisters and skin irritation and often forcing the patient to purchase increased sized shoes big enough to fit the bulky insole. Thus, there is a need in the art for a force sensing system that uses a plurality of remote sensors to obtain and compare measurements from a plurality of regions.

SUMMARY OF THE INVENTION

The present invention is an ergonomically designed force system for monitoring of weight and for activating an electronic orthosis. The system includes three independent pneumatic components that measure loads around different parts of the body. The first component is an inflatable Foot Sensor System (FSS) that is worn inside the shoe. The second component is an inflatable Knee Force System (KFS) that is worn on the anterior aspect of the knee joint. The third component is an inflatable Palm Force System (PFS) that is worn above the hand around the thenar and the hypothenar. All the components are used to correct and improve the quality of neurological rehabilitation according to Neurodevelopment Treatment (NDT) or other approaches by measuring the correct load under the palm, knee and lower leg during weight bearing (WB) treatment.

The Foot Sensor System (FFS) comprises a flexible insole that is worn inside a shoe. The insole comprises at least two pockets which may be inflated with air or filled with liquid. Each pocket is connected to a tube that, in turn, connects with a connector coupling and a pressure sensor that are remote from the insole. Each coupling contains a valve. The valves open to allow air or liquid to flow in or out of each pocket. The valves also close to block the flow of air or liquid in and out of each pocket. The pressure sensors measure the air or liquid pressure within each of the pockets in the insole, and convert the corresponding mechanical force to a suitable signal medium, usually electrical signals. In one embodiment, the insole contains a first air or liquid pocket in the heel region and a second air or liquid pocket in the forefoot region. In another preferred embodiment, the insole contains a first air or liquid pocket in the heel region and a plurality of air or liquid pockets in the forefoot region. The present invention thus provides for accurate real time monitoring of weight bearing on different regions of the foot and activation of a functional electrical stimulation (FES) system to control drop foot and normalize gait pattern.

The ergonomic design conforms to the dynamic changes in the weight during gait cycle. This contributes to the excellent comfort and high gait performance during motor activation. The foot sensor is integrated in electronic orthosis to activate the dorsi flexors and the plantar flexors for therapeutic and functional use during different parts of the gait cycle. The foot sensor can activate the electronic orthosis as a switch with on and off positions or as a load monitor on the base of pressure measurement that can improve the timing of the activation. The quick simple set-up procedure combined with the effectiveness of the dedicated treatment and the aesthetic and ergonomic design of the device will result in a high compliance rate in using the foot sensor.

The knee force system (KFS) contains at least one pocket which may be inflated with air or liquid. The pocket is connected to a tube that, in turn, connects with a pressure sensor and a connector coupling that are remote from the KFS. The pressure sensor measures the air or liquid pressure within the pocket in the KFS, and converts the corresponding mechanical force to a suitable signal medium, usually electrical signals. The present invention thus provides for accurate real time monitoring of weight bearing on different locations of the knee.

The KFS will be used in the clinics during neurological rehabilitation. Functional exercises during rehabilitation are based on normal development stages, and composed of half kneeling position and the practice of crawling and transferring from quadruped to sitting and standing which are basics and important exercises.

The palm force system (PFS) contains at least one pocket which may be inflated with air or liquid. The pocket is connected to a tube that, in turn, connects with an air pressure sensor and a connector coupling that are remote from the PFS. The pressure sensor measures the air or liquid pressure within the pocket in the PFS, and converts the corresponding mechanical force to a suitable signal medium, usually electrical signals. The present invention thus provides for accurate real time monitoring of weight bearing on different locations of the palm (Thenar and hypothenar and the heads of metacarpal bones).

Each component in the present invention can be connected to a processor that generates feedback or connected to a neuromuscular stimulation of the muscles based on the signals generated by the sensors of the present invention.

BRIEF DESCRIPTION OF THE DRAWINGS

The present invention will be better understood after reading the following detailed description of the presently preferred embodiments thereof with reference to the appended drawings, in which:

FIG. 5b illustrates a diagram of the disconnected coupling of FIG. 5a; and

DETAILED DESCRIPTION OF THE INVENTION

Figure 1:
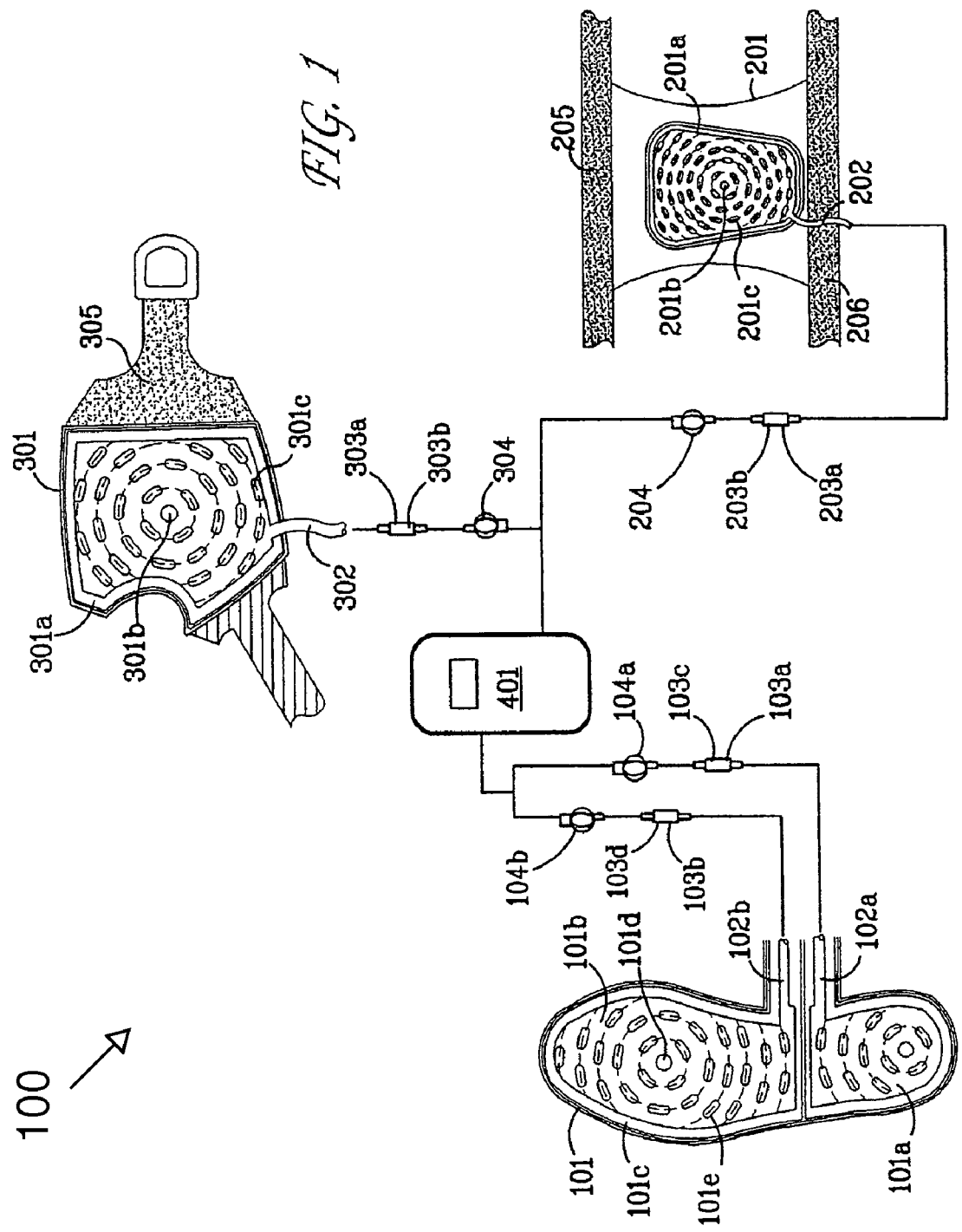
FIG. 1 illustrates a diagram of the force sensor system of the invention.

A system which meets the above-mentioned objects and provides other beneficial features in accordance with the presently preferred exemplary embodiment of the invention will be described below with reference to FIGS. 1-6. Those skilled in the art will readily appreciate that the description given herein with respect to those figures is for explanatory purposes only and is not intended in any way to limit the scope of the invention. Throughout the description, like reference numerals will refer to like elements in the respective figures.

Generally, the force sensor system comprises at least one of a foot force sensor, a palm force sensor, and a knee force sensor. Each of these individual sensors convert received pressure signals into electrical output signals representative of weight bearing on a location. The electrical output signals serve as input signals to an attached control unit of a weight bearing biofeedback system or an electrical stimulation system. Referring now to FIG. 1, force sensor system 100 comprises a foot force sensor 101, a knee force sensor 201, and a palm force sensor 301 each connected to portable control unit 401 through a tube that, in turn, connects with an air pressure sensor 104a,b, 204, and 304 and a connector coupling 103a-d, 203a,b, 303a,b. Such components are available in different sizes and are preferably suitable for left and right. The function of individual force sensors 101, 201, and 301 will be described in detail below.

1. The Foot Force Sensor

The foot force sensor comprises a flexible insole worn inside a shoe. The flexible insole contains a plurality of pockets that may be inflated with air or liquid. The air or liquid pressure in each pocket is measured by a remote pressure sensor connected to each pocket through a tube. The pressure sensors convert received pressure signals into electrical output signals representative of weight bearing on a region of the foot. The electrical output signals serve as input signals to an attached control unit of a weight bearing biofeedback system or an electrical stimulation system.

Figure 2A:
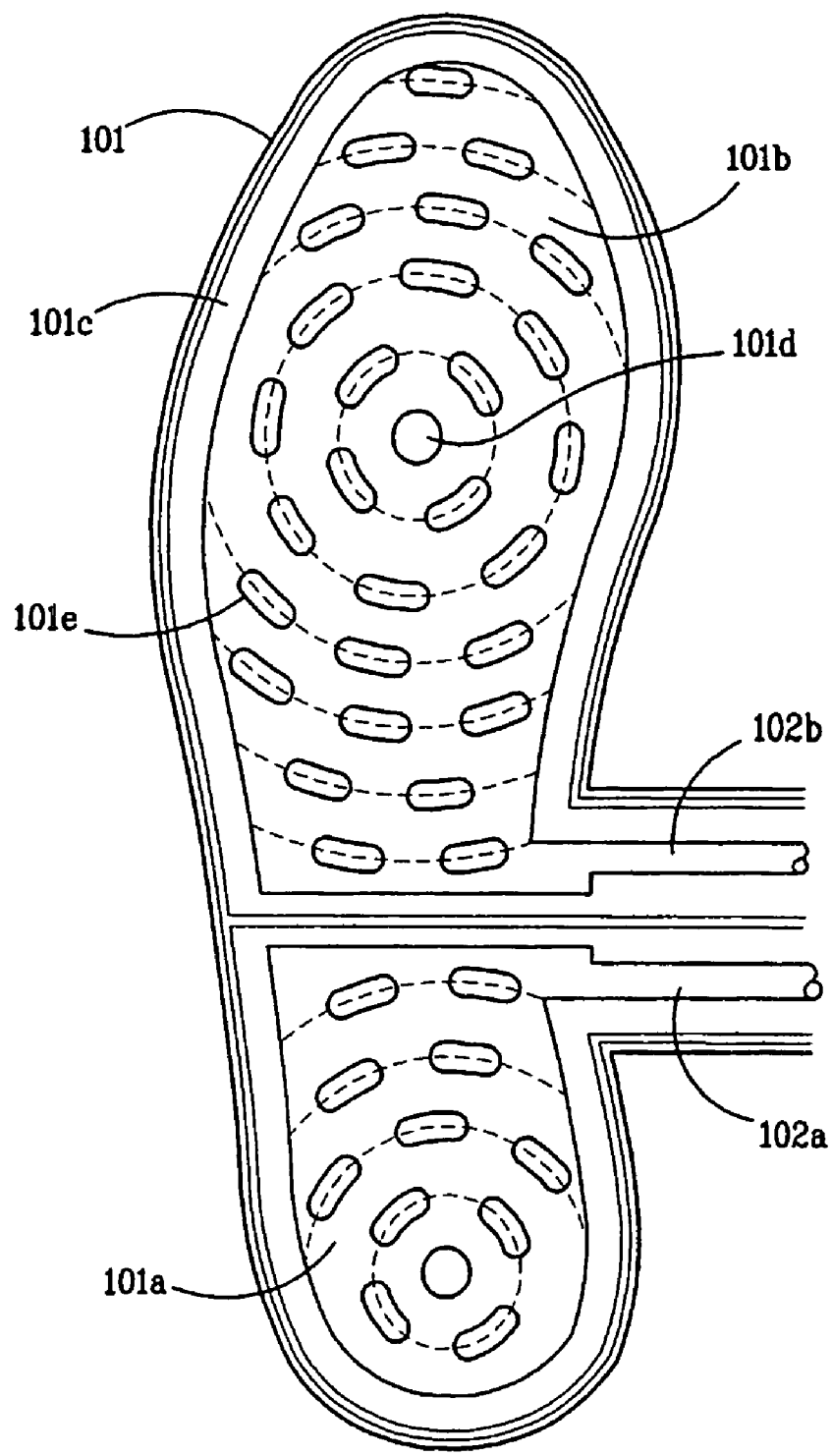
FIG. 2a illustrates a diagram of a foot force sensor with a first pocket in the heel region of the insole and a second pocket in the forefoot region.

As shown in FIG. 2a, flexible insole 101 comprises a first pocket 101a in the heel region and a second pocket 101b in the forefoot region. Insole 101 is formed of two outer layers of fabric sheets welded together using RF-welding or ultrasonic seal. The fabric sheets may be coated with polyurethane or polyvinylchloride. The material from which the insole is constructed is selected so that the rate of diffusion of the air through the barrier material of the insole will be extremely slow, the insole remaining inflated to a substantial pressure for several weeks.

The welding pattern consists of a first weld 101c around the perimeter of each of the two air pockets 101a,b and a second weld of concentric welds 101e emitting from a central weld 101d to form an internal circular passageway in each air pocket. Pockets 101 a,b are enclosed by at least two layers of translucent film. Pockets 101a,b are non-overlapping and independent. Urethane tubes 102a,b connect pockets 101a,b to couplings 103a,b,c,d and pressure sensors 104a,b.

Figure 6:
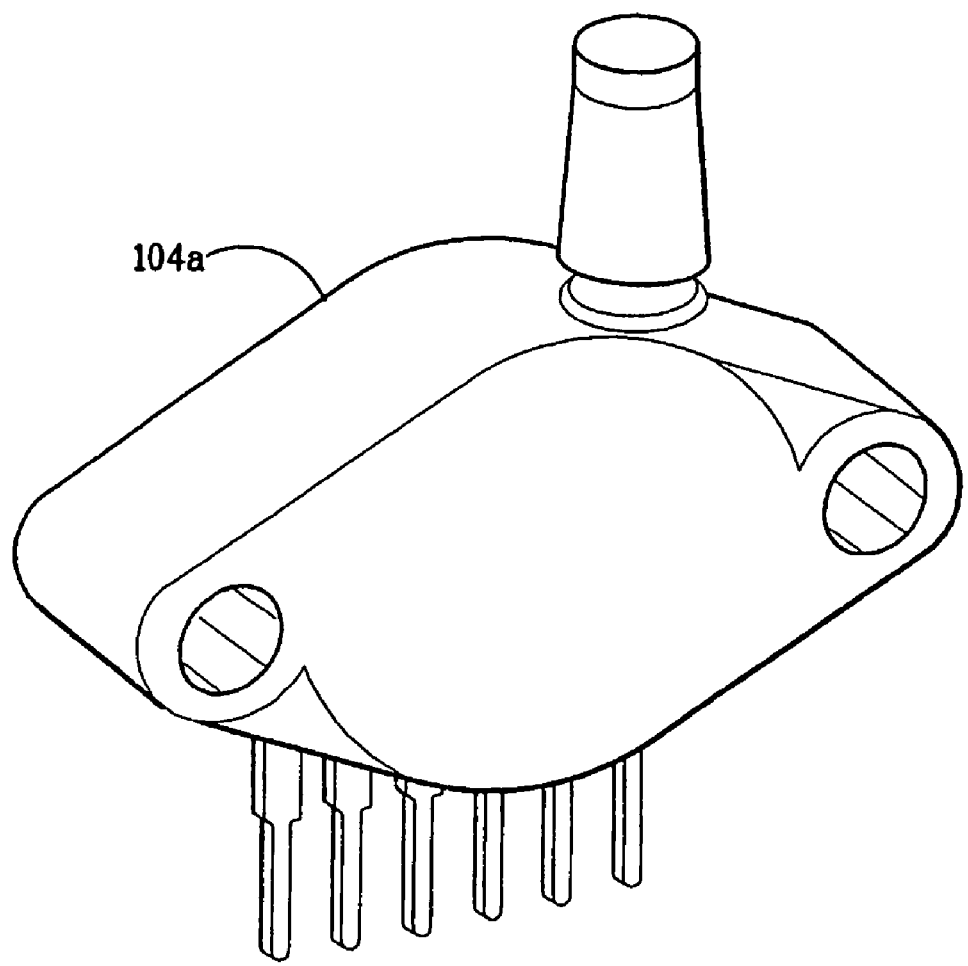
FIG. 6 illustrates a diagram of the pressure sensor.

The pressure sensors 104a,b measure the air or liquid pressure within each of the pockets 101 a,b in insole 101. Pressure sensor 104a is illustrated in FIG. 6. Pressure sensors 104a,b are preferably integrated silicone pressure sensors manufactured by Motorola as part No. MPX4250AP or any other pressure sensors disposed to convert mechanical force into electrical output signals. The electrical output signals serve as input signals to an attached control unit of a weight bearing biofeedback system or an electrical stimulation system.

Figure 2B:
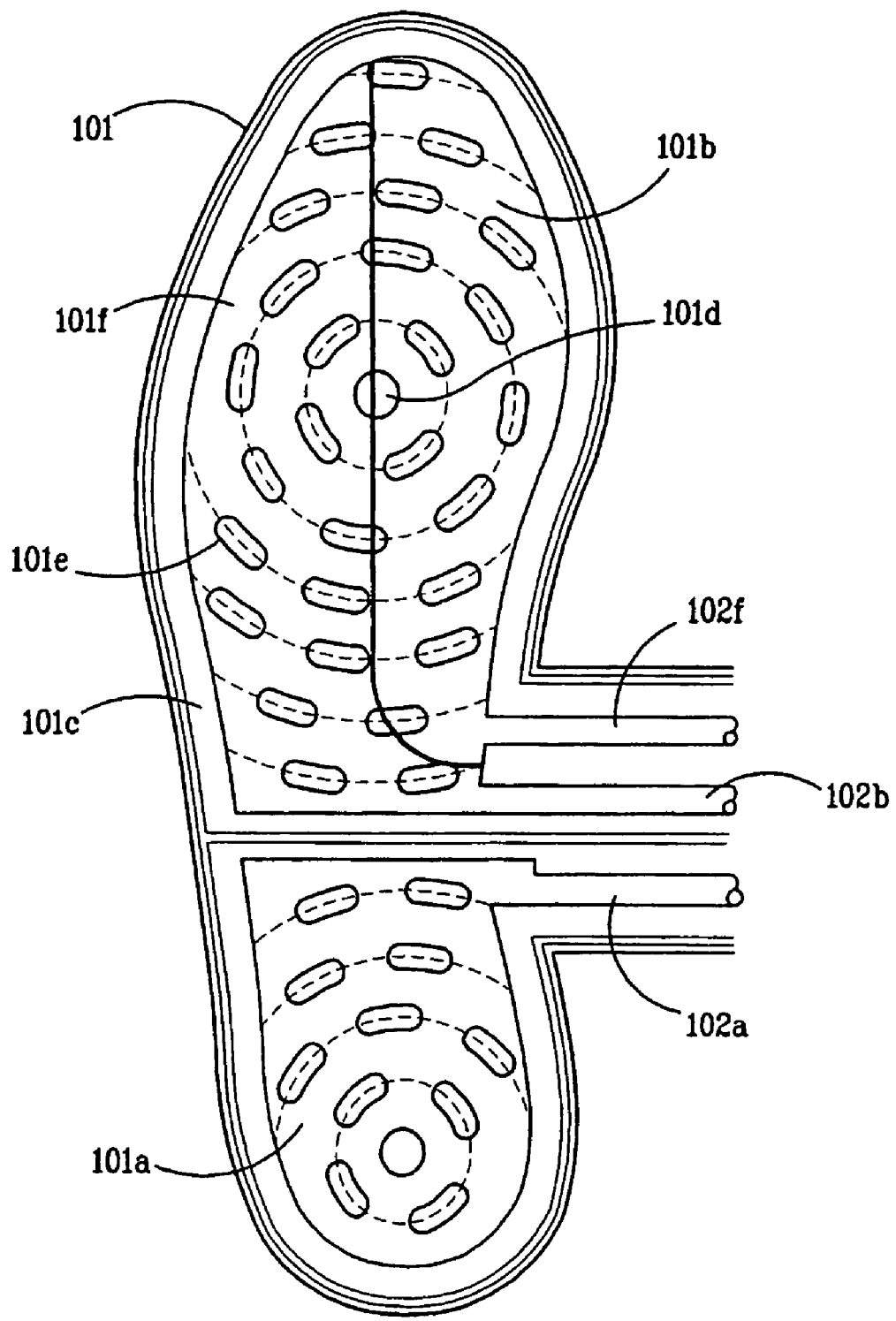
FIG. 2b illustrates a diagram of a foot force sensor with a first pocket in the heel region of the insole and two pockets in the forefoot region.

In addition to the foot force sensor comprising a single heel pocket 101a and a single forefoot pocket 101b discussed above, the foot force sensor may also comprise more than two pockets. Referring now to FIG. 2b, insole 101 comprises a first pocket 101a in the heel region and two pockets 101b,f in the forefoot region. This embodiment provides a more detailed monitoring of weight bearing on the forefoot during the forefoot push off stage of gait because the weight applied to the forefoot region of the foot is monitored in more than one area. This more detailed monitoring may be used to enable an attached stimulator to generate different stimulation to more than one area of the posterior muscles of the tibia (the calf muscles) to further improve the clearance of the foot and initiate the swing. This embodiment may also be used to monitor if too much or too little weight is being applied to different areas of the forefoot during forefoot push off. The two pockets in the forefoot region allow for measurement of the force applied to two different areas of the forefoot during the forefoot push off and the heel landing.

Figure 5A:
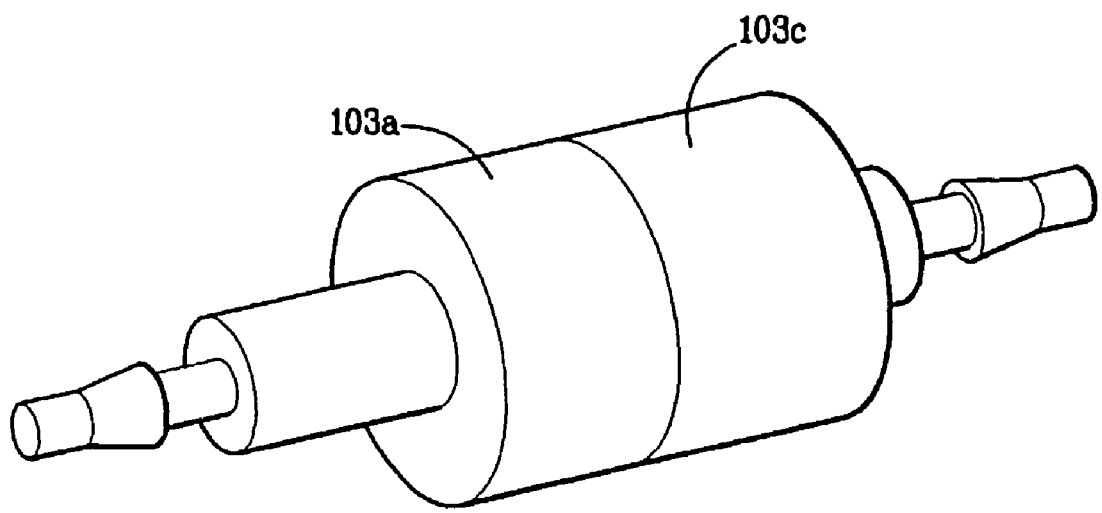
FIG. 5a illustrates a diagram of the coupling in an embodiment of the invention.
Figure 5B:
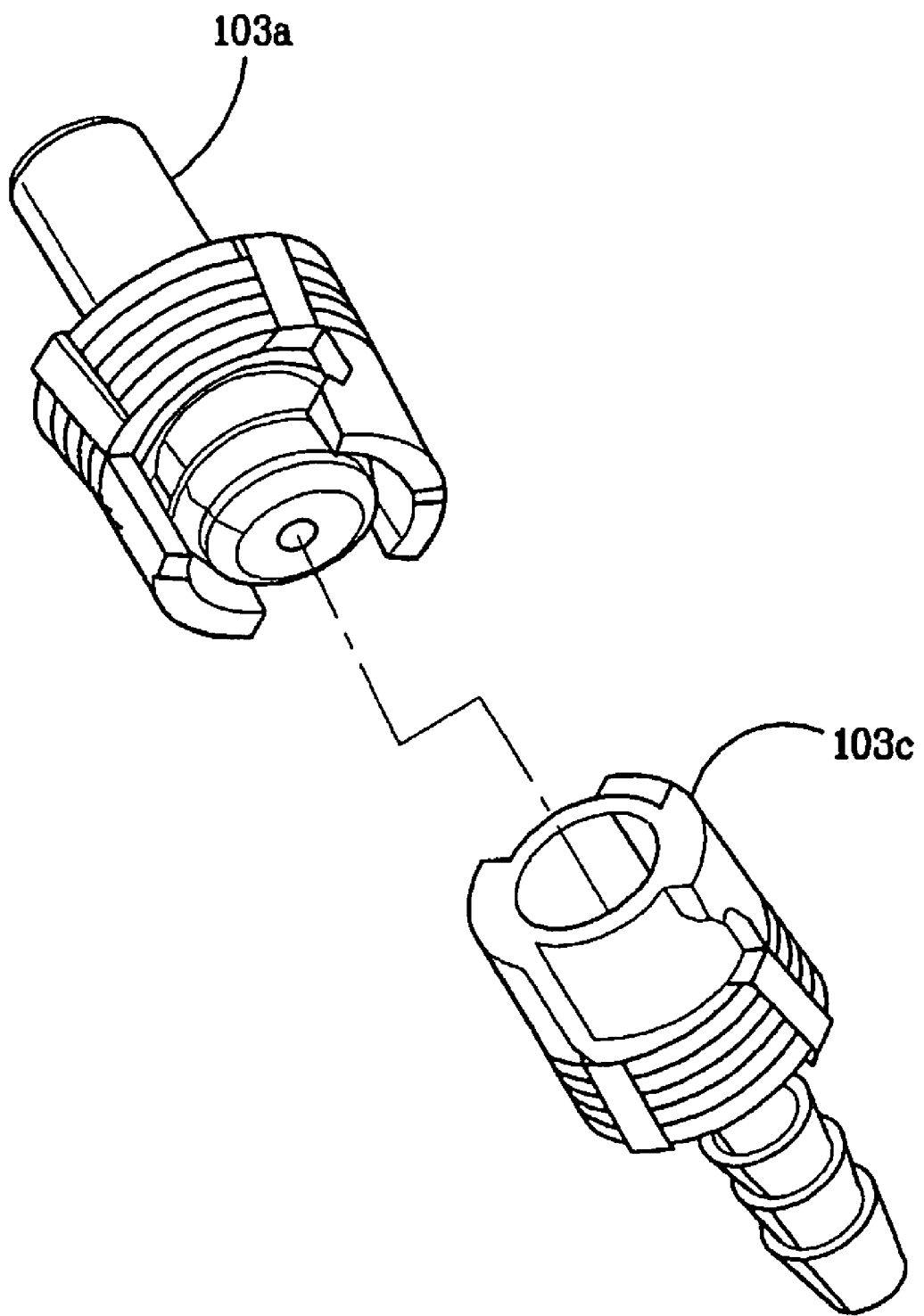

Couplings 103 a-d are quick disconnect miniature plastic couplings with a valve and a leak free o-ring seal. Couplings 103 a-d are accessible externally for easy adjustment by the therapist or by the wearer. Couplings 103 a-d may be adjusted to control three stages of operation of the foot force sensor. First, the valves are opened to allow inflation of the pockets. During the inflation stage, the user may open the valve and connect an inflation device such as a simple pump or an injection pistol. Once the pockets are inflated to a desired volume, the inflation device may be detached. Second, the valves are closed to block the flow of air or liquid to and from the pockets. Third, the couplings 103 a,c and 103 b,d are reconnected by twist and the valves are reopened to allow passage of air or liquid from the pockets to the pressure sensors 104 a,b for closed system operation. FIG. 5a illustrates a diagram of coupling 103 a,c in the connected position. FIG. 5b illustrates a diagram of coupling 103 a,c in the disconnected position.

The closed system operation stage may be used to control an electric orthosis when the foot force sensor is connected to an electrical stimulation system. The closed system operation stage works according to Boyle's Law, which states that, for a closed system, the change in volume from a first time to a second time $(V_t/V_{t+1})$ is inversely proportional to the corresponding change in pressure $(P_t/P_{t+1})$. The closed system operation stage may be divided into five sub-stages of the gait cycle: initial contact, loading response, midstance, push off, and swing. During the first sub-stage of the closed system operation stage (V=$V_1$ and P=$P_1$), the heel landing will increase the force applied to heel pocket 101a causing the first sub-stage volume, $V_1$ in the heel air pocket 101a to decrease. Thus, during the initial contact, heel region pressure sensor 104a will detect an increase in pressure to the heel pocket 101a and will relay a corresponding electrical signal to an attached rehabilitation system or to the micro-controller of an attached electronic orthosis. During the second sub-stage of the closed system operation stage, the loading response (V=$V_2$ and P=$P_2$), the entire foot is placed on the ground. During the third sub-stage of the closed system operation stage, midstance (V=$V_3$ and P=$P_3$), weight is shifted from the heel region to the forefoot region causing the third sub-stage volume, $V_3$ in the forefoot air pocket 101b to decrease. Thus, during midstance, both forefoot pressure sensor 104a and heel pressure sensor 104b will detect an increase in pressure to forefoot pocket 101a and heel pocket 101b, respectively, and will relay a corresponding electrical signal to an attached rehabilitation system or to the micro-controller of an attached electronic orthosis. During the fourth sub-stage of the closed system operation stage, push-off (V=$V_4$ and P=$P_4$), the foot is lifted and only the forefoot has contact with the ground. The push-off phase begins with the heel rise and continues until the other foot strikes the ground. Throughout the push-off phase, the body weight moves ahead of the forefoot. During the fifth sub-stage of the closed system operation stage, swing (V=$V_5$ and P=$P_5$), the foot is in the air.

Figure 2C:
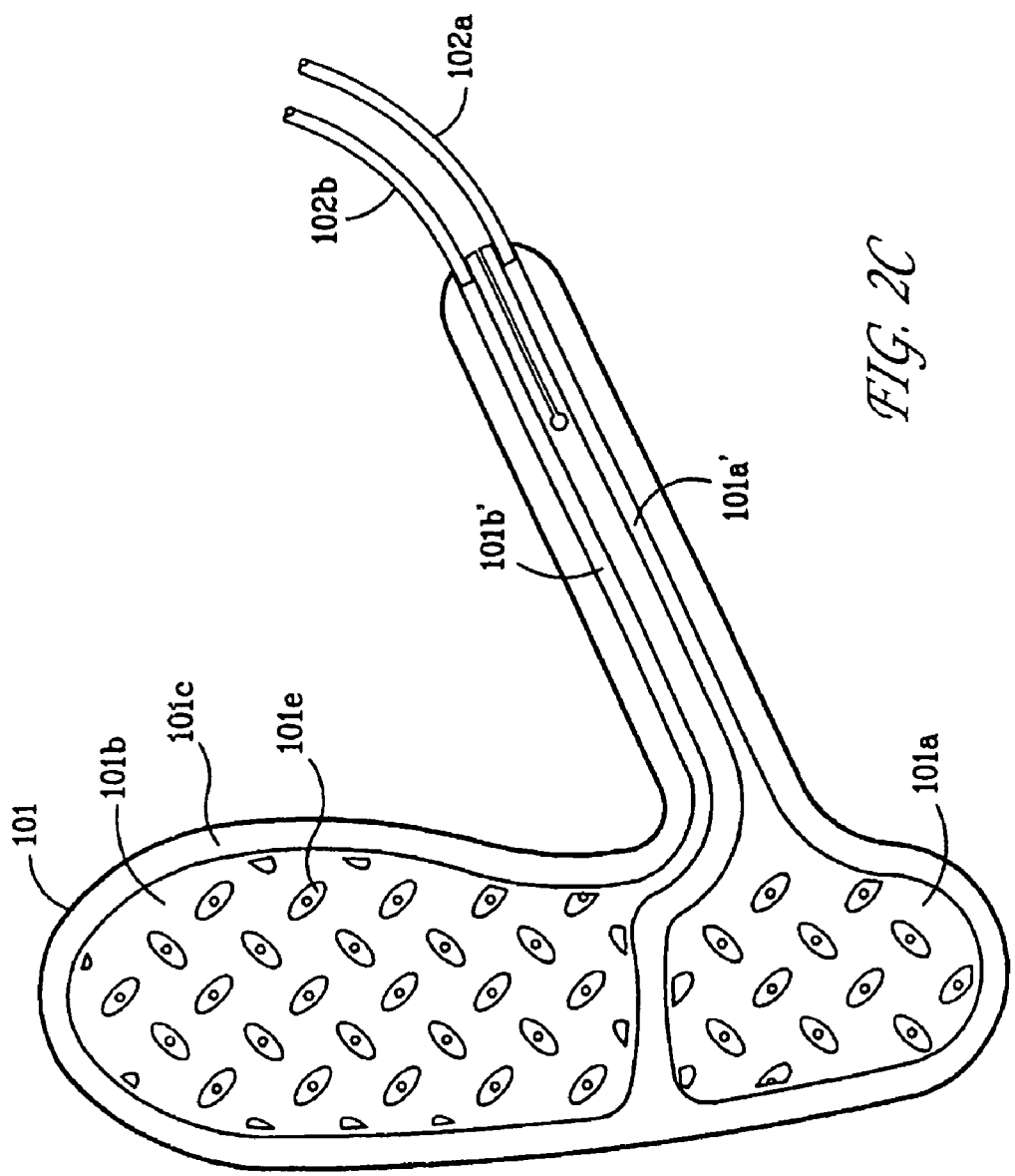
FIG. 2c illustrates a diagram of a foot force sensor with pocket extensions.

An alternative embodiment of the foot force sensor in accordance with the present invention is shown in FIG. 2c. The welding pattern consists of a first weld 101c around the perimeter of each of the two air pockets 101a,b and a second weld of parallel rows of welds 101e along the longitudinal axis of the insole 101. The rows alternate between welds 101e positioned at a 45 degree angles and 135 degree angles in relation to the longitudinal axis.

The alternative embodiment also includes pocket extensions 101a' and 101b', which connect pockets 101a and 101b to tubes 102a and 102b, respectively. Pocket extensions 101a' and 101b' may be formed of the same coated fabric material as pockets 101 and 101b. Pocket extensions 101a' and 101b' may be, for example, approximately ten to fifteen centimeters in length and may wrap around the ankles.

Tubes 102a and 102b may be, for example, approximately two to three centimeters in length and may be inserted approximately one centimeter into pocket extensions 101a' and 101b'. Tubes 102a and 102b may connect pocket extension 101a' and 101b' to couplings 103a,b,c,d and pressure sensors 104a,b, which may be comprised in a control unit box fastened around the ankle.

In yet another alternative embodiment, the foot force sensor shown in FIG. 2c may include three pockets, with two pockets in the forefoot region. Each such pocket may include corresponding pocket extensions which connect to corresponding couplings and pressure sensors.

2. The Knee Force Sensor

The knee force sensor comprises a wrap that is worn on the anterior aspect of the knee joint. The wrap comprises two bands for tightly securing the wrap on the anterior aspect of the knee joint. The wrap further comprises at least one pocket that may be inflated with air or liquid. The air or liquid pressure in the pocket is measured by a remote pressure sensor connected to the pocket through a tube. The pressure sensor converts received pressure signals into electrical output signals representative of weight bearing on the knee. The electrical output signals serve as input signals to an attached control unit a weight bearing biofeedback system.

Figure 3:
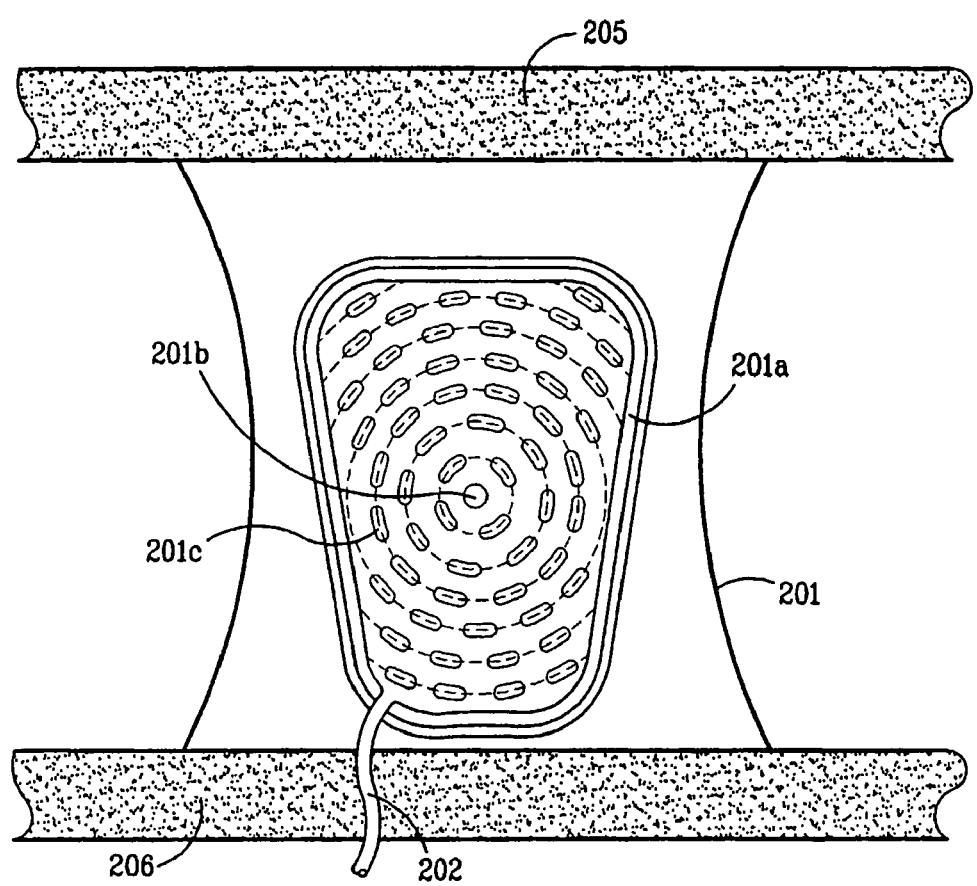
FIG. 3 illustrates a diagram of a knee force sensor in accordance with the invention.

As shown in FIG. 3, wrap 201 comprises bands 205, 206 for tightly securing the wrap on the anterior aspect of the knee joint. Wrap 201 is formed of two outer layers of fabric sheets welded together using RF-welding or ultrasonic seal. The fabric sheets may be coated with polyurethane or polyvinylchloride. The material from which the wrap is constructed is selected so that the rate of diffusion of the air through the barrier material of the insole will be extremely slow, the insole remaining inflated to a substantial pressure for several weeks. The welding pattern consists of a perimeter weld 201a and a second weld 201c of concentric circles of welds originating at the center of wrap 201. Wrap 201 is enclosed by at least two layers of translucent film. Urethane tube 202 connects wrap 201 to coupling 203a,b and pressure sensor 204. Pressure sensor 204 is preferably an integrated silicone pressure sensor manufactured by Motorola as part No. MPX4250AP or any other pressure sensor disposed so as to measure the air or liquid pressure within the pocket and to convert the corresponding mechanical force into electrical output signals. The electrical output signals serve as input signals to an attached control unit of a weight bearing biofeedback system.

Coupling 203 a,b is a quick disconnect miniature plastic coupling with a valve and a leak free o-ring seal. Coupling 203 a,b is accessible externally for easy adjustment by the therapist or by the wearer. Coupling 203 a,b may be adjusted to control three stages of operation of the knee force sensor. First, the valve is opened to allow inflation of the pocket. During the inflation stage, the user may open the valve and connect an inflation device such as a simple pump or an injection pistol. Once the pocket is inflated to a desired volume, the inflation device may be detached. Second, the valve is closed to block the flow of air or liquid to and from the pocket. Third, the coupling 203 a,b is reconnected by twist and the valve is reopened to allow passage of air or liquid from the pocket to the pressure sensor 204 for closed system operation.

The knee force system will be used in the clinics during neurological rehabilitation. Functional exercises during rehabilitation are based on normal development stages, and composed of half kneeling position and the practice of crawling and transferring from quadruped to sitting and standing which are basics and important exercises.

3. The Palm Force Sensor

Figure 4:
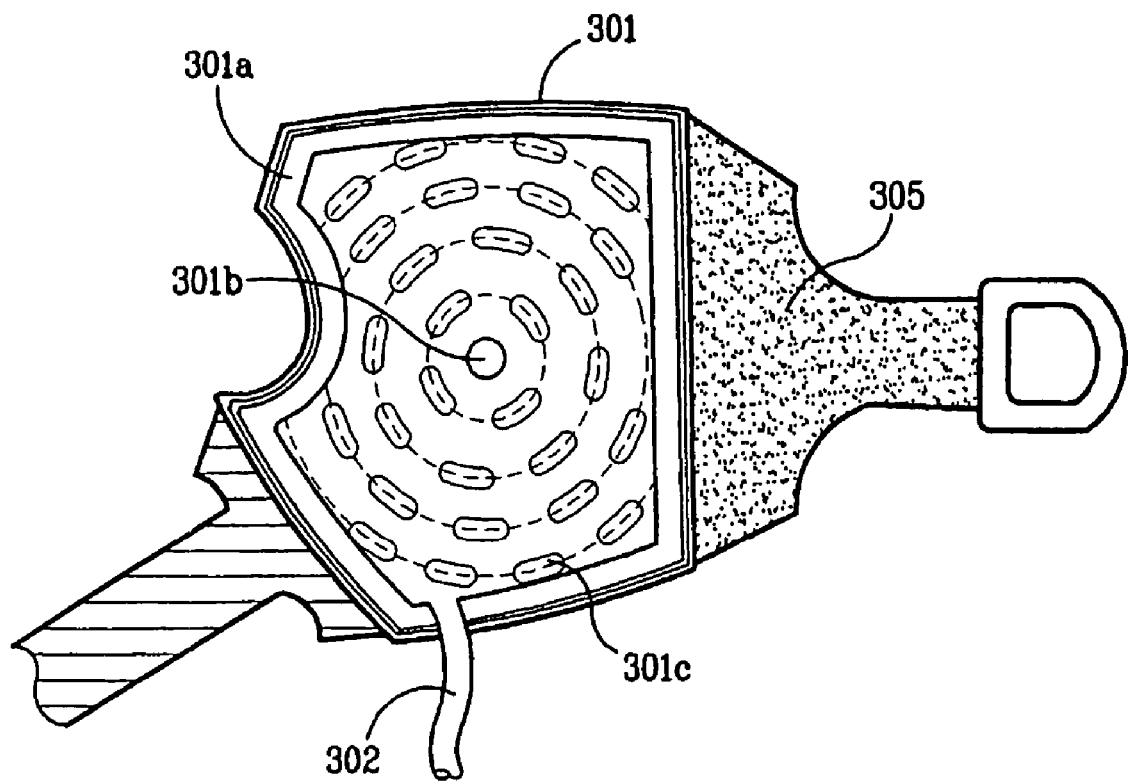
FIG. 4 illustrates a diagram of a palm force sensor in accordance with the invention.

The palm force sensor comprises a wrap that is worn above the hand around the thenar and the hypothenar. The wrap comprises a band for tightly securing the wrap around the thenar and the hypothenar. The wrap further comprises at least one pocket that may be inflated with air or liquid. The air or liquid pressure in the pocket is measured by a remote pressure sensor connected to the pocket through a tube. The pressure sensor converts received pressure signals into electrical output signals representative of weight bearing on the palm. The electrical output signals serve as input signals to an attached control unit a weight bearing biofeedback system. Referring now to FIG. 4, wrap 301 comprises band 305 for tightly securing the wrap around the thenar and the hypothenar. Wrap 301 is formed of two outer layers of fabric sheets welded together using RF-welding or ultrasonic seal. The fabric sheets may be coated with polyurethane or polyvinylchloride. The material from which the wrap is constructed is selected so that the rate of diffusion of the air through the barrier material of the insole will be extremely slow, the insole remaining inflated to a substantial pressure for several weeks. The welding pattern consists of a perimeter weld 301a and a second weld 301c of concentric circles of welds originating at the center of wrap 301. Wrap 301 is enclosed by at least two layers of translucent film. Urethane tube 302 connects wrap 301 to coupling 303a,b and pressure sensor 304. Pressure sensor 304 is preferably an integrated silicone pressure sensor manufactured by Motorola as part No. MPX4250AP or any other pressure sensor disposed so as to measure the air or liquid pressure within the pocket and to convert the corresponding mechanical force into electrical output signals. The electrical output signals serve as input signals to an attached control unit of a weight bearing biofeedback system.

Coupling 303 a,b is a quick disconnect miniature plastic coupling with a valve and a leak free o-ring seal. Coupling 303 a,b is accessible externally for easy adjustment by the therapist or by the wearer. Coupling 303 a,b may be adjusted to control three stages of operation of the knee force sensor. First, the valve is opened to allow inflation of the pocket. During the inflation stage, the user may open the valve and connect an inflation device such as a simple pump or an injection pistol. Once the pocket is inflated to a desired volume, the inflation device may be detached. Second, the valve is closed to block the flow of air or liquid to and from the pocket. Third, the coupling 303 a,b is reconnected by twist and the valve is reopened to allow passage of air or liquid from the pocket to the pressure sensor 304 for closed system operation.

The pressure sensors of the foot, knee, and palm force sensor systems set forth above with reference to FIGS. 2-4 generate electrical output signals that serve as input signals to central processing unit 401 of FIG. 1. Dynamic weight input signals are transmitted from the pressure sensors to the control unit 401 for processing and guiding the patient by feedback to increase or decrease the load or for activation of an electronic orthosis to prevent drop-foot. The output of dynamic control unit 401 consists of data that is sent to a personal computer (PC) and to a visual mode stimulator, an audio mode stimulator, and a mechanical vibration mode stimulator. The PC and mode stimulators generate visual feedback from the PC display, visual feedback from a wireless LCD, audio feedback, and/or mechanical vibration feedback. Such feedback prompts the patient to shift the balance of weight on the limb and/or adjust his or her gait or standing posture.

It is to be understood that the apparatus and method of operation taught herein are illustrative of the invention. Those skilled in the art will appreciate that, although the force sensing system of FIG. 1 comprises a foot force sensor, a knee force sensor, and a palm force sensor, the force sensing system of the present invention may comprise any of those individual force sensors alone or in combination. Furthermore, the insole of FIGS. 2a,b,c may be divided into any number of pockets in the heel and forefoot region. These and other modifications may readily be devised by those skilled in the art without departing from the spirit or scope of the invention. All such modifications are intended to be included within the scope of the appended claims.

We claim:

1. A force sensor system for use in monitoring weight bearing at a location on a person, comprising:
    a plurality of independent, non-overlapping pockets inflated with air or liquid, said pockets forming the interior of at least one flexible pouch placed at or near said location, wherein said at least one flexible pouch comprises two outer layers of fabric sheets, said outer layers of sheets being welded together in a welding pattern using a sealing agent said welding pattern comprising a weld around the perimeter of each pocket and a weld of concentric circles of elliptical welds originating from the center of each pocket;
    a plurality of tubes, wherein at least one tube allows flow of air or liquid in and out of each of the pockets to a location remote from the pouch; and
    a plurality of pressure sensors remote from the pouch connected to said pockets through said tubes, wherein each pressure sensor is disposed to detect the pressure applied to at least one pocket.

2. A sensor system as in claim 1, wherein
    each pressure sensor converts received pressure signals to electrical output signals representative of the weight bearing on the location, further comprising a control unit that receives the electrical output signals as input signals and provides feedback to affect movement at said location, said control unit being part of one of a weight bearing biofeedback system and an electrical stimulation system.

3. A system as in claim 2 further comprising a plurality of valves remote from said pockets connected to said pockets through said tubes, said valves open to allow inflation and deflation of said pockets and closing to allow closed system operation of said pockets.

4. A system as in claim 2, wherein said at least one flexible pouch comprises at least one of a flexible insole worn inside a shoe, a flexible wrap worn around a knee, and a flexible wrap worn around a palm.

5. A system as in claim 4, wherein the flexible insole contains a first inflatable pocket in the heel region of the insole and a second inflatable pocket in the forefoot region of the insole.

6. A system as in claim 4, wherein the flexible wrap worn around a knee comprises two adhesive strips for tightly securing the wrap on the anterior aspect of the knee joint.

7. A system as in claim 4, wherein the flexible wrap worn around a palm comprises two straps and a latch for tightly securing the wrap around the thenar and the hypothenar.

8. A system as in claim 2, wherein said weight bearing biofeedback system generates stimulating feedback signals to muscles in response to the input signals.

9. A system as in claim 2, wherein said input signals identify specific stages of a gait cycle of the foot and the electrical stimulation system uses the input signals to activate an electronic orthosis.

10. A system as in claim 1, wherein said outer layers of fabric sheets comprise a fabric base and a polyurethane coating.

11. A system as in claim 1, wherein said outer layers of fabric sheets comprise a fabric base and a polyvinylchloride coating.

12. A system as in claim 1, wherein said sealing agent comprises one of an RF-weld and an ultrasonic seal.

13. A force sensor system as in claim 1, wherein said pockets comprise at least two layers of translucent film.

14. A system as in claim 1, further comprising:
    a controller that receives electrical output signals from said pressure sensors as input signals, said controller activating a stimulator to deliver stimulation to a first muscle group in response to input signals from a heel pressure sensor and activating said stimulator to deliver stimulation to a second muscle group in response to input signals from a forefoot pressure sensor.

15. A system as in claim 14, wherein the degree of said stimulation by said stimulator is proportional to the pressure measurements obtained by said pressure sensors.

16. A system as in claim 14, wherein said first muscle group is the anterior muscles of the tibia.

17. A system as in claim 14, wherein said second muscle group is the posterior muscles of the tibia.

18. A system as in claim 2, wherein the feedback includes audio, visual and/or mechanical vibration feedback that prompts a patient to shift the balance of weight on the location and/or to adjust the patient's gait or standing posture.

* * * * *